(12) United States Patent
Kirschman

(10) Patent No.: US 9,457,119 B2
(45) Date of Patent: Oct. 4, 2016

(54) FLUID STERILIZATION SYSTEM

(71) Applicant: David Louis Kirschman, Dayton, OH (US)

(72) Inventor: David Louis Kirschman, Dayton, OH (US)

(73) Assignee: Aerobiotix, Inc., Dayton, OH (US)

( * ) Notice: Subject to any disclaimer, the term of this patent is extended or adjusted under 35 U.S.C. 154(b) by 568 days.

(21) Appl. No.: 13/838,367

(22) Filed: Mar. 15, 2013

(65) Prior Publication Data

US 2014/0157989 A1    Jun. 12, 2014

Related U.S. Application Data

(60) Provisional application No. 61/735,623, filed on Dec. 11, 2012.

(51) Int. Cl.
*A61L 9/20* (2006.01)
*B01D 46/00* (2006.01)

(52) U.S. Cl.
CPC ............. *A61L 9/20* (2013.01); *B01D 46/0028* (2013.01)

(58) Field of Classification Search
CPC ................................ A61L 9/20; B01D 46/0028
See application file for complete search history.

(56) References Cited

U.S. PATENT DOCUMENTS

| | | |
|---|---|---|
| 3,683,638 A | 8/1972 | Devon |
| 3,744,216 A | 7/1973 | Halloran |
| 3,804,942 A | 4/1974 | Kato et al. |
| 3,812,370 A | 5/1974 | LaViolette |
| 3,988,131 A | 10/1976 | Kanazawa et al. |
| 4,118,191 A | 10/1978 | Bohnensieker |
| 4,210,429 A | 7/1980 | Golstein |
| 4,225,323 A | 9/1980 | Zarchy et al. |
| 4,244,710 A | 1/1981 | Burger |
| 4,437,007 A * | 3/1984 | Koslow ................. G01T 1/1644 250/366 |
| 4,531,956 A | 7/1985 | Howorth |
| 4,621,195 A | 11/1986 | Larsson |
| 4,694,179 A | 9/1987 | Lew et al. |
| 4,737,173 A | 4/1988 | Kudirka et al. |

(Continued)

FOREIGN PATENT DOCUMENTS

| | | |
|---|---|---|
| DE | 19614893 | 10/1997 |
| EP | 1491218 | 12/2004 |
| WO | 0160419 A1 | 8/2001 |

OTHER PUBLICATIONS

Mohammadian, "Effect of TiO2 Nanoparticles on the Spectral Characterisitics of Rhodamine 6G Fluoresence Emission", Mar. 2012, ICNS4, All Pages.*

*Primary Examiner* — Amber R Orlando
*Assistant Examiner* — Britanny Precht
(74) *Attorney, Agent, or Firm* — Jacox, Meckstroth & Jenkins

(57) ABSTRACT

A fluid filtration system is shown. The fluid filtration system utilizes a one-piece or multiple piece containers having a plurality of radiation-transmissible media adapted to receive light, such as ultraviolet light, white light or other wavelength light. The radiation-transmissible media are situated in the container and at least one or a plurality of radiation sources, such as ultraviolet lamps, are situated in an array in proximity to the radiation-transmissible media. The radiation-transmissible media interrupts the flow and velocity of the fluid stream passing through the container to extend the duration of radiation for any contaminants and also provide enlarged surface areas for the contaminants to be received and ultimately exposed to the radiation. In one example, the radiation-transmissible media may be tubular or spherical sections that are hollow or solid and made of quartz.

45 Claims, 12 Drawing Sheets

(56) References Cited

U.S. PATENT DOCUMENTS

| | | | |
|---|---|---|---|
| 4,749,385 | A | 6/1988 | Brunner et al. |
| 4,750,917 | A | 6/1988 | Fujii |
| 4,787,922 | A | 11/1988 | Kulitz |
| 4,835,983 | A | 6/1989 | Chandler, Jr. et al. |
| 4,900,344 | A | 2/1990 | Lansing |
| 4,954,320 | A * | 9/1990 | Birmingham .......... B01D 53/32 422/184.1 |
| 4,959,010 | A | 9/1990 | Burtscher et al. |
| 4,990,313 | A | 2/1991 | Pacosz |
| 5,004,483 | A | 4/1991 | Eller et al. |
| 5,225,167 | A | 7/1993 | Wetzel |
| 5,233,975 | A | 8/1993 | Choate |
| 5,240,478 | A | 8/1993 | Messina |
| 5,399,319 | A | 3/1995 | Schoenberger et al. |
| 5,601,786 | A | 2/1997 | Monagan |
| 5,616,172 | A | 4/1997 | Tuckerman et al. |
| 5,616,532 | A * | 4/1997 | Heller .................... B01J 35/002 502/242 |
| 5,656,242 | A | 8/1997 | Morrow et al. |
| 5,681,374 | A | 10/1997 | Von Glehn |
| 5,761,908 | A | 6/1998 | Oas et al. |
| 5,772,738 | A | 6/1998 | Muraoka |
| 5,891,399 | A * | 4/1999 | Owesen .................... A61L 9/20 422/121 |
| 5,997,619 | A | 12/1999 | Knuth et al. |
| 6,053,968 | A | 4/2000 | Miller |
| 6,182,461 | B1 | 2/2001 | Washburn et al. |
| 6,248,235 | B1 | 6/2001 | Scott |
| 6,322,614 | B1 | 11/2001 | Tillmans |
| 6,544,485 | B1 | 4/2003 | Taylor |
| 6,613,277 | B1 | 9/2003 | Monagan |
| 6,656,424 | B1 | 12/2003 | Deal |
| 6,797,042 | B2 | 9/2004 | LaFerriere et al. |
| 6,911,177 | B2 | 6/2005 | Deal |
| 7,251,953 | B2 | 8/2007 | Wetzel et al. |
| 7,318,856 | B2 | 1/2008 | Taylor et al. |
| 7,323,065 | B2 | 1/2008 | Fencl et al. |
| 7,531,141 | B2 | 5/2009 | Descotes et al. |
| 7,854,900 | B2 | 12/2010 | Takeda et al. |
| 7,892,501 | B2 | 2/2011 | Parker et al. |
| 8,168,122 | B2 | 5/2012 | Lee |
| 8,236,236 | B2 | 8/2012 | Garner |
| 8,252,099 | B2 | 8/2012 | Worrilow |
| 2002/0085947 | A1 | 7/2002 | Deal |
| 2002/0144601 | A1 | 10/2002 | Palestro et al. |
| 2002/0172627 | A1 | 11/2002 | Aoyagi |
| 2003/0012703 | A1 | 1/2003 | Lee |
| 2003/0086831 | A1 | 5/2003 | Horton |
| 2003/0198568 | A1 | 10/2003 | Fencl |
| 2005/0000365 | A1 * | 1/2005 | Nelsen ...................... A61L 9/16 96/224 |
| 2006/0057020 | A1 | 3/2006 | Tufo |
| 2007/0041882 | A1 | 2/2007 | Roseberry et al. |
| 2009/0041617 | A1 | 2/2009 | Lee |
| 2009/0041632 | A1 | 2/2009 | Day et al. |
| 2012/0183443 | A1 | 7/2012 | Hurley |
| 2012/0183444 | A1 | 7/2012 | Lee |
| 2012/0282135 | A1 | 11/2012 | Trapani |
| 2014/0044590 | A1 | 2/2014 | Trapani |

\* cited by examiner

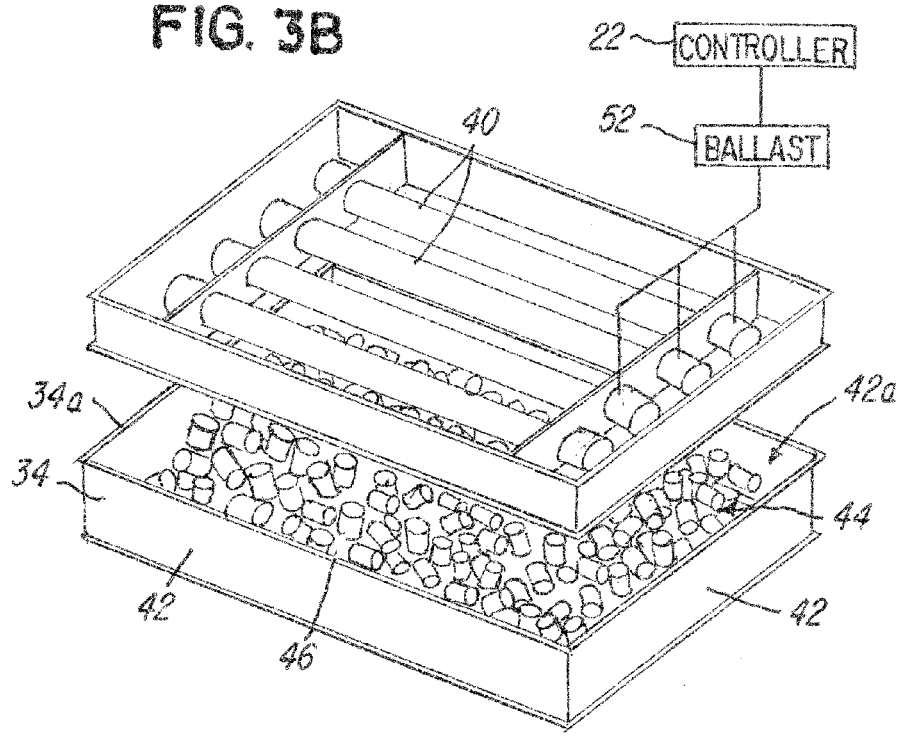
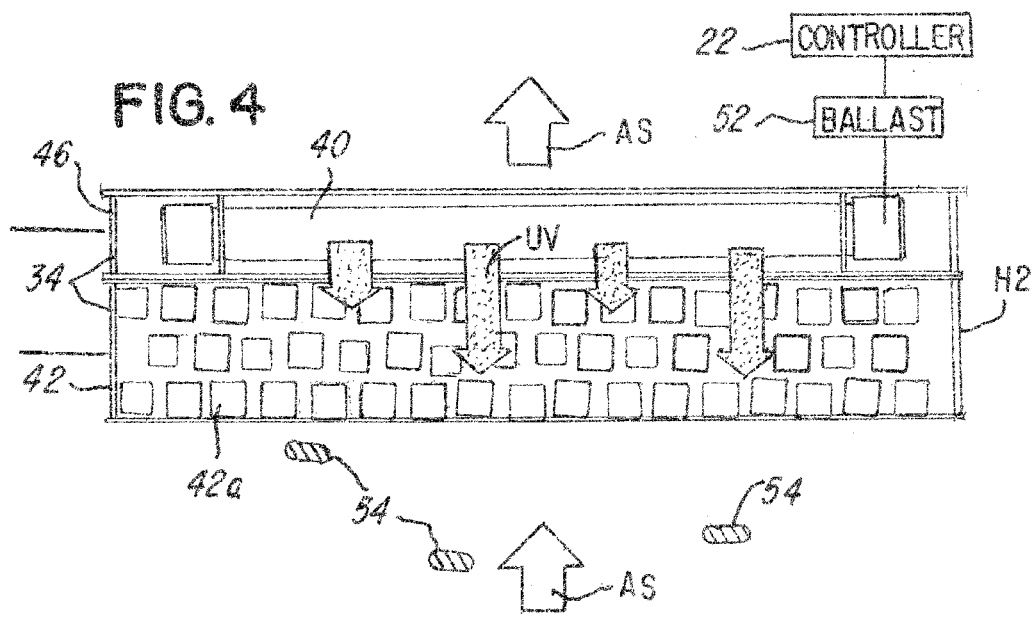

5A

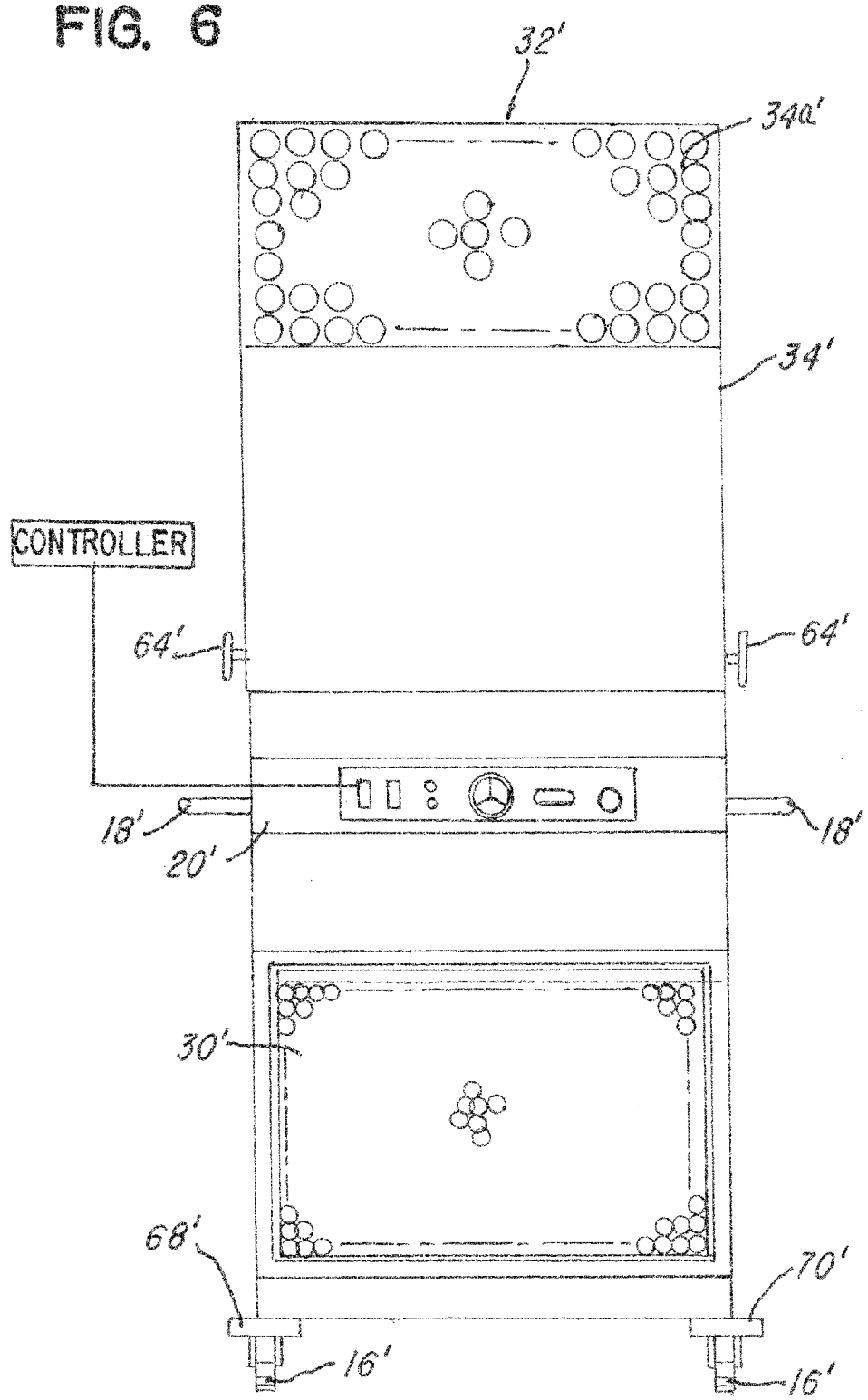

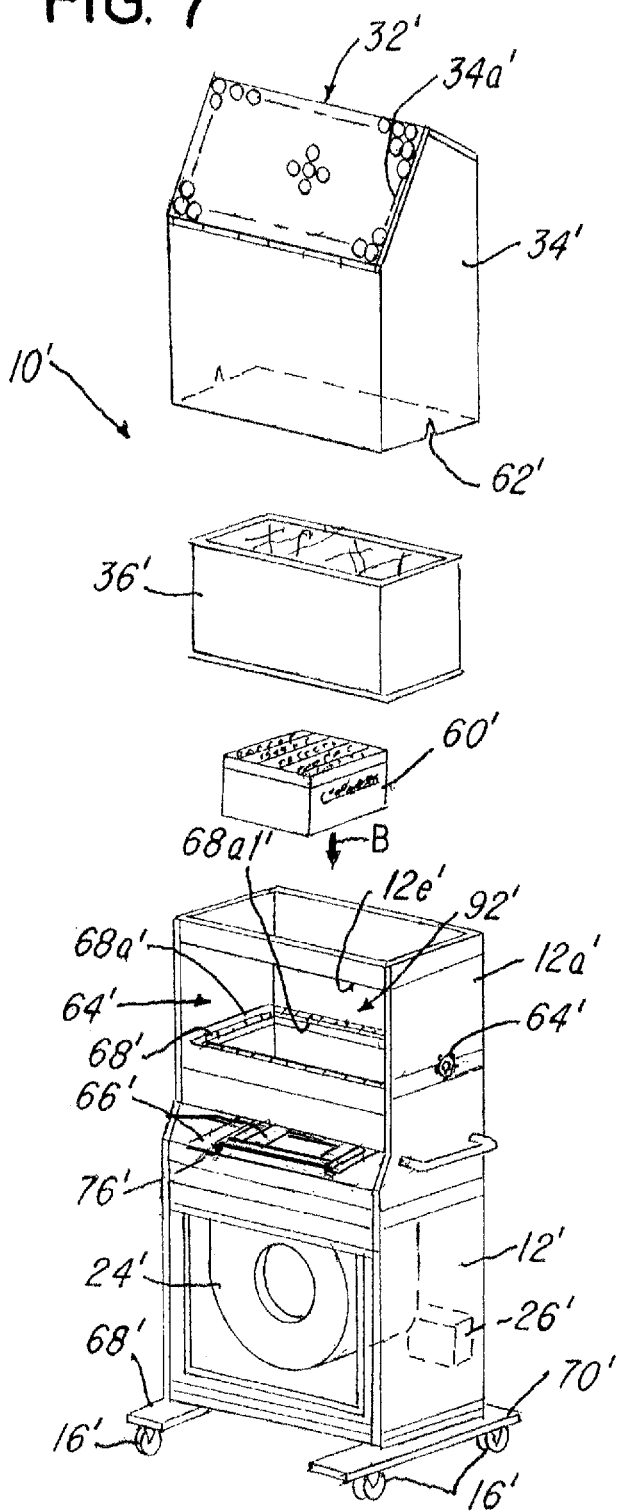

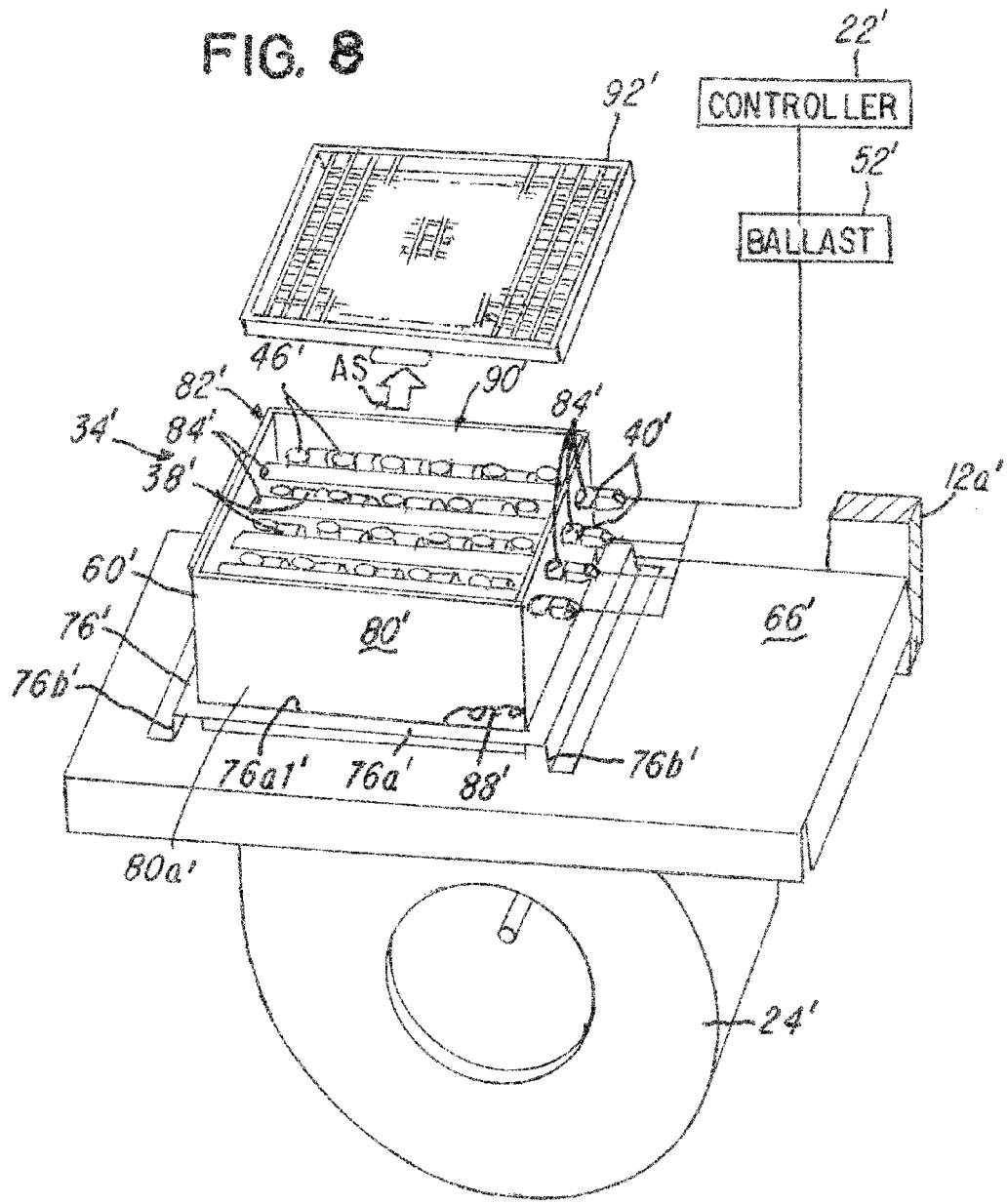

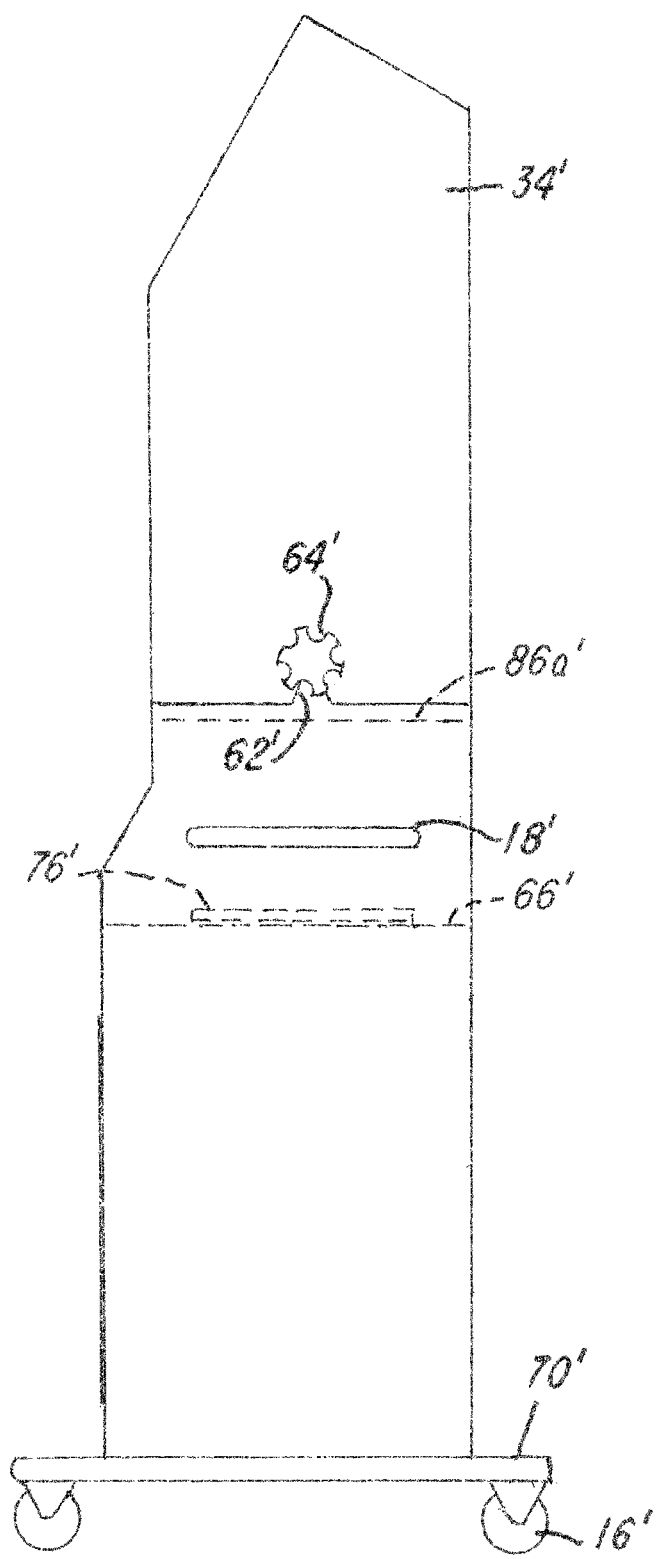

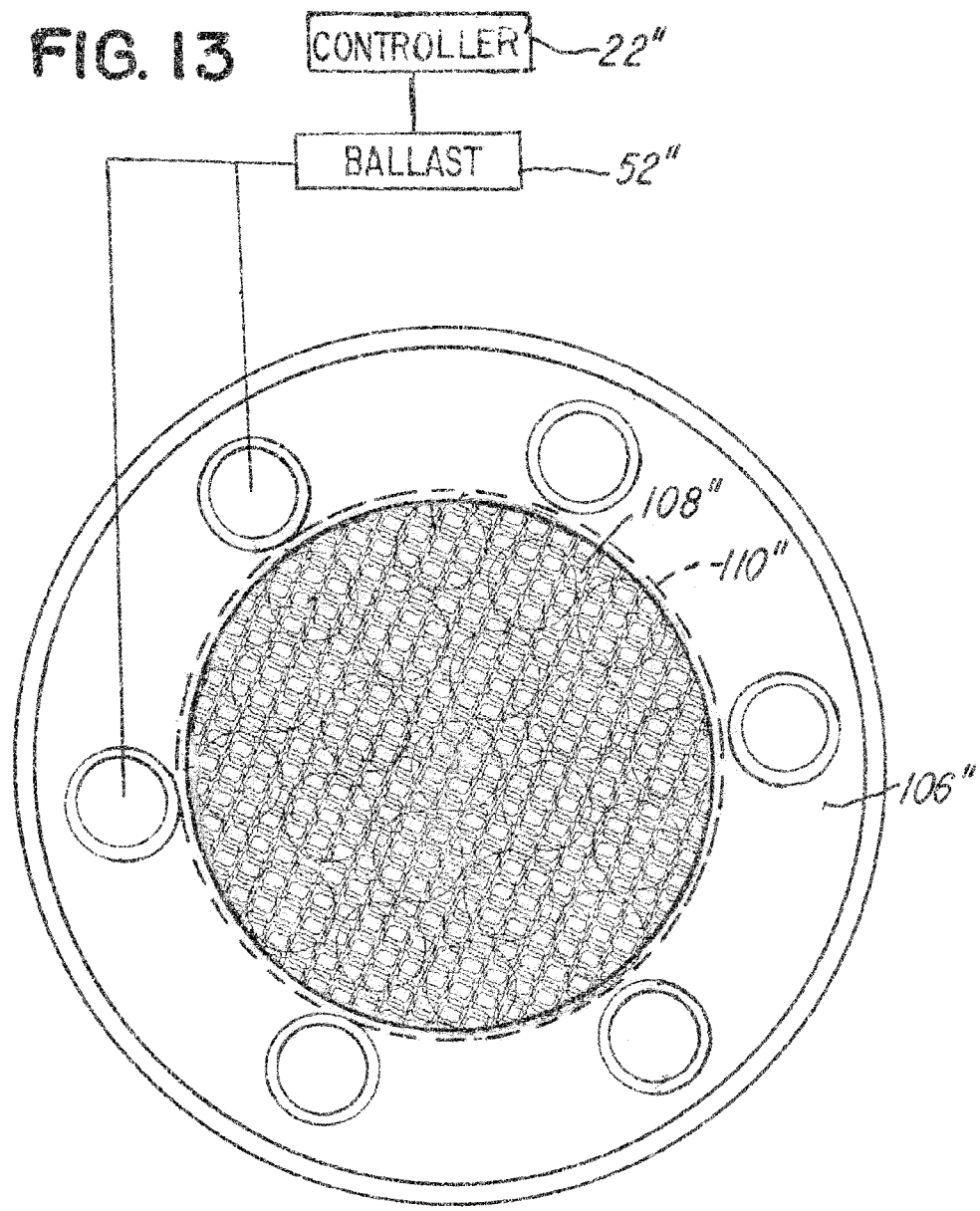

FLUID STERILIZATION SYSTEM

CROSS-REFERENCE TO RELATED APPLICATION

The present application claims priority to provisional U.S. Application Ser. No. 61/735,623 filed Dec. 11, 2012, to which Applicant claims the benefit of the earlier filing date. This application is incorporated herein by reference and made a part hereof.

BACKGROUND OF THE INVENTION

1. Field of the Invention

This invention relates to sterilization and, more particularly, to a sterilization system that utilizes radiation-transmissible media to facilitate disinfecting a fluid stream.

2. Background of the Invention

There is a critical need to clean and sterilize room fluid in hospitals physician offices and operating room settings. Fluid borne bacteria and viruses cause disease and infection, particularly in health-care settings. Recently, there has been increased scrutiny placed upon the prevalence of hospital acquired infections, including surgical wound infections. Surprisingly, little is done to attempt to disinfect fluid at the room level within these settings. What is needed is a fluid sterilization system which will effectively eliminate bacteria and viruses on a room-sized scale. In order to achieve these objectives, improvements must be made in current fluid sterilization technologies which will allow effective continuous disinfection of large fluid volumes within a portable unit.

Several mechanisms have been devised to filter and disinfect fluid. In some hospital-based systems, ultraviolet light is placed within ventilation ducts. These systems have important disadvantages in that the fluid flows past the UV sources at a high rate of speed, limiting the disinfection power of the UV light. Additionally, such static systems cannot be relocated to areas of increased infective potential. Furthermore, mechanical filters, such as commonly employed HEPA systems, have limited effectiveness upon viruses and small bacteria.

Ultraviolet radiation is known to be effectively virucidal and bactericidal. The amount of disinfective effect of ultraviolet radiation is directly proportional to radiation intensity and duration of exposure. Several portable fluid cleaner systems have been developed which utilize UV light, however such systems move fluid directly past ultraviolet sources, which limits concentration of the radiation and minimizes length of exposure. Furthermore, such systems have no mechanism to capture organisms during the UV treatment process to maximize organism exposure. Additionally, standard systems simply draw and release fluid in close proximity, which limits device effectiveness.

SUMMARY OF THE INVENTION

What is needed, therefore, is an improved fluid sterilization system which accomplishes several key objectives:
  slowing the fluid path during an irradiation process;
  providing a mechanism to disperse, slow, and capture organisms during the irradiation process;
  providing a mechanism to concentrate the UV or radiation energy within a flow-through disinfection vessel; and
  maintaining safety and portability appropriate for use in a health-care setting.

One object of the invention is to provide a sterilization system having radiation-transmissible media for facilitating disinfection.

Another object of the invention is to provide radiation-transmissible media in different shapes, sizes and made of different materials.

Another object of the invention is to provide a fluid filtration system that is easy to service and access.

Another object of the invention is to provide a fluid filtration system that utilizes a container for housing radiation-transmissible media and a radiation source situated adjacent thereto.

Still another object of the invention is to provide a container for housing radiation-transmissible media and for also housing a radiation source, such as UV lamps.

In one aspect, one embodiment of the invention comprises a fluid sterilization system comprising a container, radiation-transmissible media situated in the container, and a radiation source, the radiation-transmissible media being adapted to provide both mechanical filtration by physically capturing organisms as they are carried through the container in an fluid stream and substantially simultaneously permitting transmission of radiation from the radiation source through the radiation-transmissible media, the radiation being an appropriate amount to disinfect the fluid stream and at least one surface of the radiation-transmissible media.

In another aspect, another embodiment of the invention comprises a filtration assembly for use in a fluid filtration system, the filtration assembly comprising a container, and radiation-transmissible media situated in the container, the container being adapted to be situated in the fluid filtration system in proximate relationship to a radiation source to provide both mechanical filtration by physically capturing organisms as they are carried through the container in a fluid stream and substantially simultaneously permitting transmission of radiation from the radiation source through the radiation-transmissible media, the radiation being an appropriate amount to disinfect the fluid stream and at least one surface of the radiation-transmissible media.

These and other objects and advantages of the invention will be apparent from the following description, the accompanying drawings and the appended claims.

BRIEF DESCRIPTION OF THE DRAWINGS

FIG. 3B is another exploded view of the embodiment shown in FIG. 2 illustrating a random arrangement of radiation-transmissible media in a container;

FIG. 4 is a view illustrating the radiation source and contaminants flowing through the fluid filtration assembly of FIG. 2;

FIG. 6 is a view of another embodiment of a fluid filtration system;

FIG. 7 is an exploded view of the embodiment shown in FIG. 6;

FIG. 8 is an exploded view showing a one-piece container and radiation source assembly in accordance with the embodiment shown in FIG. 6;

FIG. 9 is a right side view of the embodiment shown in FIG. 6 illustrating an elongated hood and knobs for supporting the hood on a housing;

FIGS. 11-13 are various views of a generally circular housing or container having the radiation-transmissible media therein and surrounded by a generally circular array of radiation lamps.

DETAILED DESCRIPTION OF PREFERRED EMBODIMENTS

Figure 11:
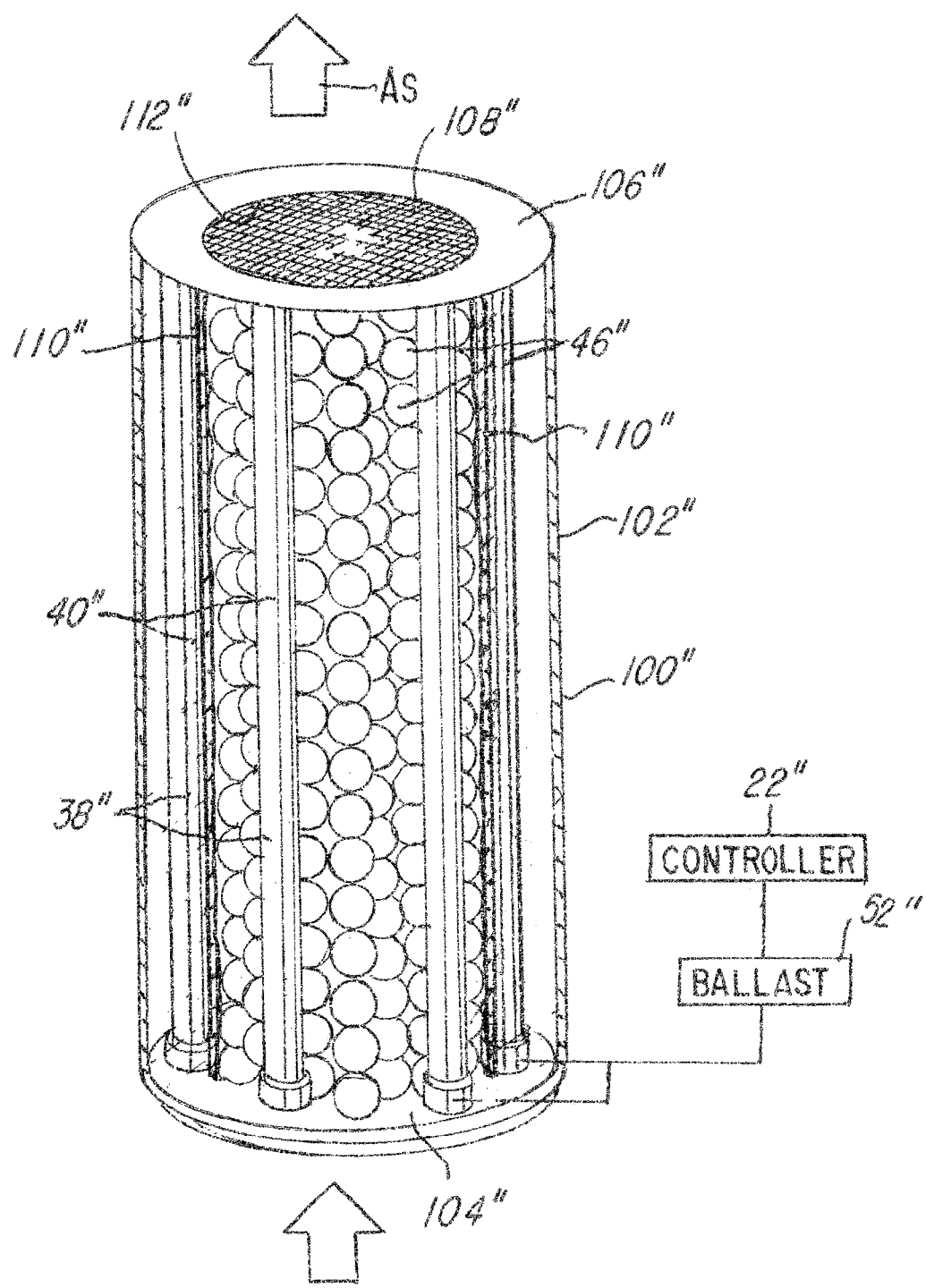
Figure 12:
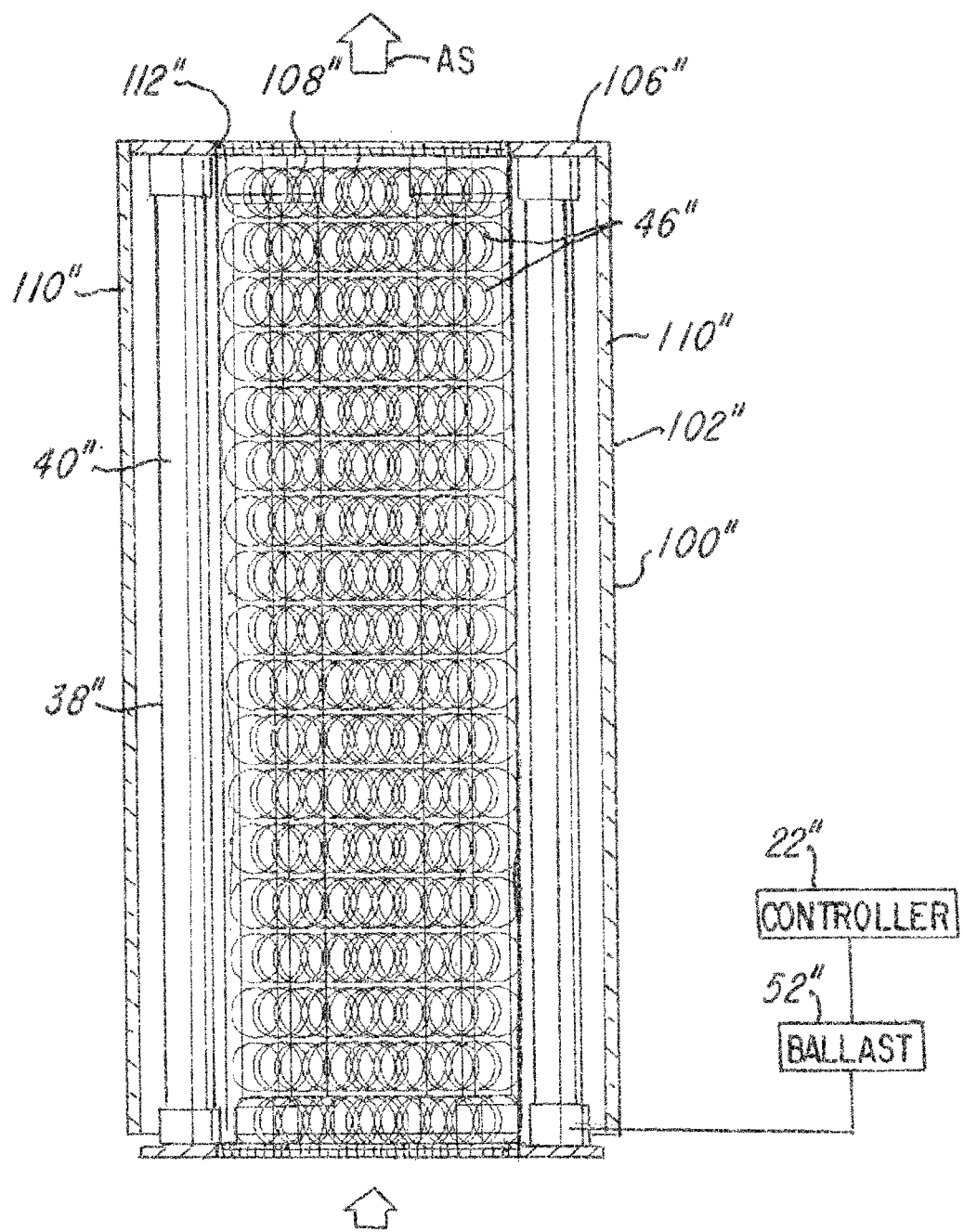

Referring now to FIGS. 1-13, embodiments of a fluid sterilization system 10 are shown. A first embodiment of the fluid sterilization system 10 is shown in FIGS. 1-5 and a second embodiment is shown in FIGS. 6-10. FIGS. 11-13 illustrate another embodiment of a fluid filtration assembly. For ease of illustration and description, like parts in each of the embodiments are identified with the like part numbers, except a prime mark ("'") and a double prime mark ("''") have been added to the second embodiments of FIGS. 6-10 and the third embodiment in FIGS. 11-13, respectively.

Referring now to FIGS. 1-5, the first embodiment of the fluid sterilization system 10 comprises a mobile housing unit 12 that is mobile and easily moved by hand. In the illustration being described, the mobile housing unit 12 is movable by hand using at least one or a plurality of handles 18 that are conventionally secured to a housing wall 12a of the mobile housing unit 12.

The mobile housing unit 12 comprises a control panel 20 and a controller 22 for controlling the mobile housing unit 12. The control panel 20 comprises a system and cooperates to provide means for programming and controlling the operation of the mobile housing unit 12. The mobile housing unit 12 comprises a base frame or support 14 comprising at least one or a plurality of fans or blowers 24 that are conventionally mounted to the base frame or support 14 inside the mobile housing unit 12 and are driven by at least one or a plurality of blower motors 26 that is electrically coupled to and under the control of the controller 22.

Note that the housing wall 12a of the mobile housing unit 12 is generally rectangular, made of stainless steel in the illustration being described and extends generally upwardly or vertically from the base frame or support 14. The housing wall 12a is specifically designed to provide a vertical duct for drawing fluid into an intake 28, through at least or a plurality of filters described later herein and ultimately through an outlet or exit 32. The mobile housing unit 12 and housing wall 12a comprises a removable first grate or mesh screen 30 that is conventionally mounted to the housing wall 12a with screws (not shown) and that covers the inlet or intake 28 for introduction of contaminated fluid into the fluid sterilization system 10. At the exit 32, a removable cover or hood 33 is removably situated on a top edge 12b of the housing wall 12a and about an interior support wall 12c as shown.

Figure 1:
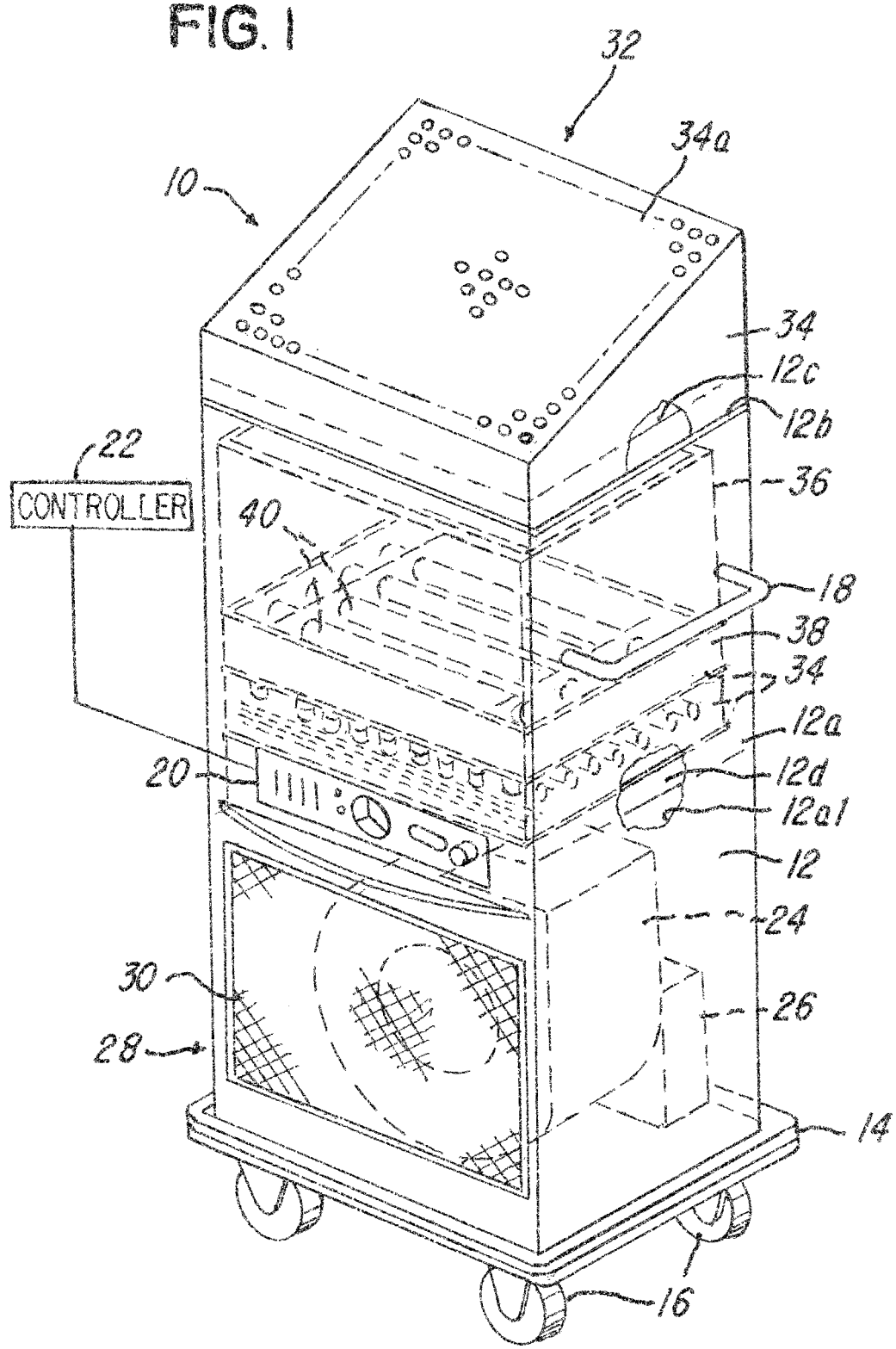
FIG. 1 is a perspective view of one embodiment of a fluid filtration system in accordance with one embodiment of the invention.

In the embodiment shown in FIG. 1, note that the cover or hood 33 is generally trapezoidal when viewed from a side and has a top surface 33a that is perforated to provide or define a grate, mesh wall or surface that defines the exit 32 through which fluid may pass.

The fluid sterilization system 10 further comprises at least one or a plurality of fluid filtration assemblies 34 and at least one or a plurality of conventional high-efficiency particulate air or HEPA filters 36. In one illustrative embodiment, the at least one or a plurality of fluid filtration assemblies 34 and the at least one or a plurality of HEPA filters 36 are separated by at least one or a plurality of radiation sources 38 which in the embodiment being described comprises at least one or a plurality of ultra violet lamps 40 as shown.

One advantageous feature of the fluid sterilization system 10 is the ease with which the at least one or a plurality of fluid filtration assemblies 34 and the at least one or a plurality of HEPA filters 36 may be inserted, changed and/or serviced. In this regard, note that the mobile housing unit 12 has a support surface or shelf 12d (shown only in FIGS. 1 and 2 for ease of illustration). Note that the support surface or shelf 12d has a generally rectangular opening (not shown) that is slightly smaller than the fluid filtration assembly 34 so that fluid may pass through the support surface or shelf 12d and through the fluid filtration assembly 34, past the lamps 40, through the HEPA filter 36 and ultimately through the exit 32 of the fluid sterilization system 10.

Figure 2:
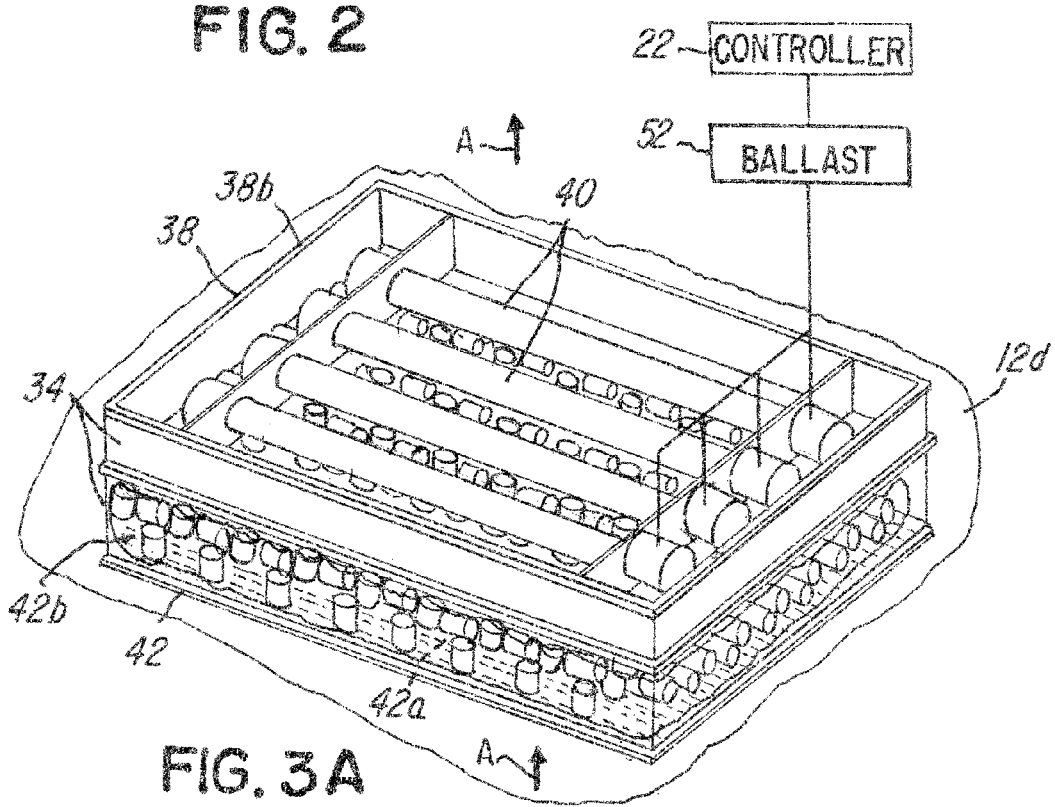
FIG. 2 is a fragmentary view illustrating features of a fluid filtration assembly in accordance with one embodiment of the invention.

One feature of the illustration being described is the ease with which the fluid filtration assembly 34 and HEPA filter 36 may be inserted into the mobile housing unit 12 or changed. In the embodiment of FIGS. 1-4, note that the fluid filtration assembly 34, radiation source 38 and the HEPA filter 36 are stacked as shown. The edges of each of these components may have a reminder (not shown), such as tongue and groove configuration, to make proper alignment and mounting of the components easier. Alternatively, and as illustrated in FIGS. 2-3B, the fluid filtration assembly 34 and the radiation source 38 comprise generally flat planar top surfaces or edges 34a and 38a that are adapted and sized to complement the shape of each other and mate so that the fluid filtration assembly 34, radiation source 38 and HEPA filter 36 may be stacked as shown. FIGS. 6-10 illustrate another embodiment where the radiation source 38 and the fluid filtration assembly 34 are provided in one housing or assembly, which will be described later herein.

Referring back to FIGS. 1-5, note that the fluid filtration assembly 34 comprises a generally rectangular container 42 having a perforated floor 42a that is adapted to permit fluid to flow through the container 42. In the illustration being described and as described later herein, contaminated fluid flows from a bottom of the container 42 through the perforated floor 42a in the direction of arrow A in FIG. 2 into and through the container 42.

Figure 3A:
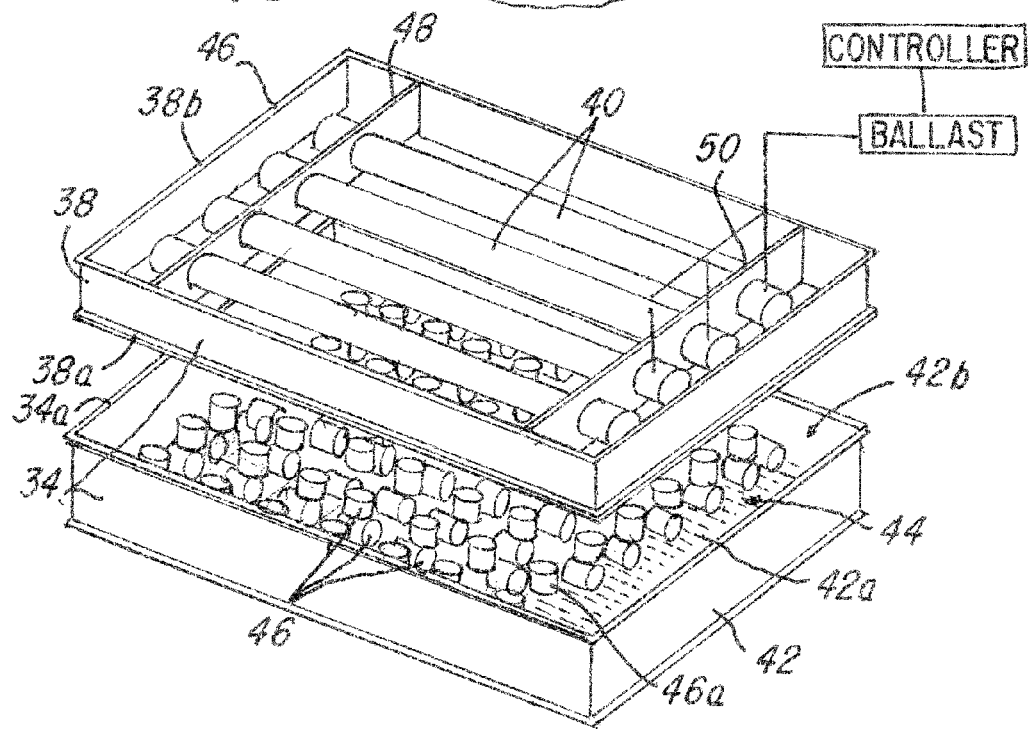
FIG. 3A is an exploded view of the embodiment shown in FIG. 2.

The generally rectangular container 42 comprises a generally rectangular vertical wall 42b (FIG. 3A) that defines a storage area 44 for receiving radiation-transmissible media 46. The radiation-transmissible media 46 are adapted to transmit radiation. In one embodiment, the radiation-transmissible media 46 is transparent media, such as glass or quartz, as mentioned herein. In the illustration being described, the radiation-transmissible media 46 may be arranged in a pattern as illustrated in FIGS. 2 and 3A or alternatively, may be arranged randomly or "poured into" the storage area 44 so that they are randomly arranged as illustrated in FIG. 3B. In a preferred embodiment, the radiation-transmissible media 46 is placed or poured into the storage area 44 and randomly arranged.

The radiation source 38 comprises a generally rectangular frame or edge 38a having a plurality of interior walls 48 and 50 which receive and support the plurality of ultraviolet lamps 40 as shown. The plurality of ultraviolet lamps 40 are coupled to a ballast 52 which in turn is coupled to and under the control of the controller 22 as shown. Although the radiation source 38 is illustrated comprising four lamps, it should be understood that it could comprise more or fewer lamps if desired.

After the radiation-transmissible media 46 is situated in the storage area 44 of the generally rectangular container 42, a bottom aligning edge 38a1 of the radiation source 38 is situated or arranged in proximate relationship on the generally rectangular container 42 on the top surface or edge 34a, as illustrated in FIGS. 2 and 4.

Figure 5:
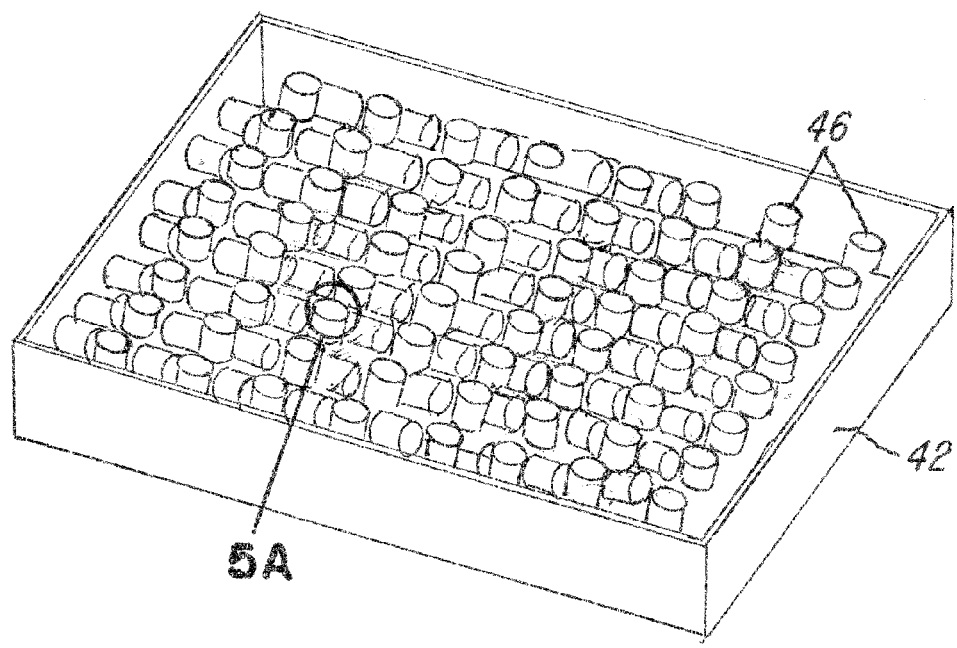
FIG. 5 is a view illustrating a container with radiation-transmissible media arranged in a non-random or predetermined order, with the container shown in fragmentary form to emphasize that it could comprise any polygonal shape.
Figure 5A:
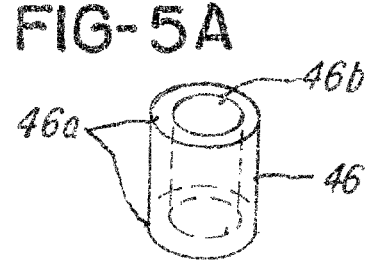
FIG. 5A is an enlarged view of a radiation-transmissible media in the form of tubular cylinder quartz.
Figure 10:
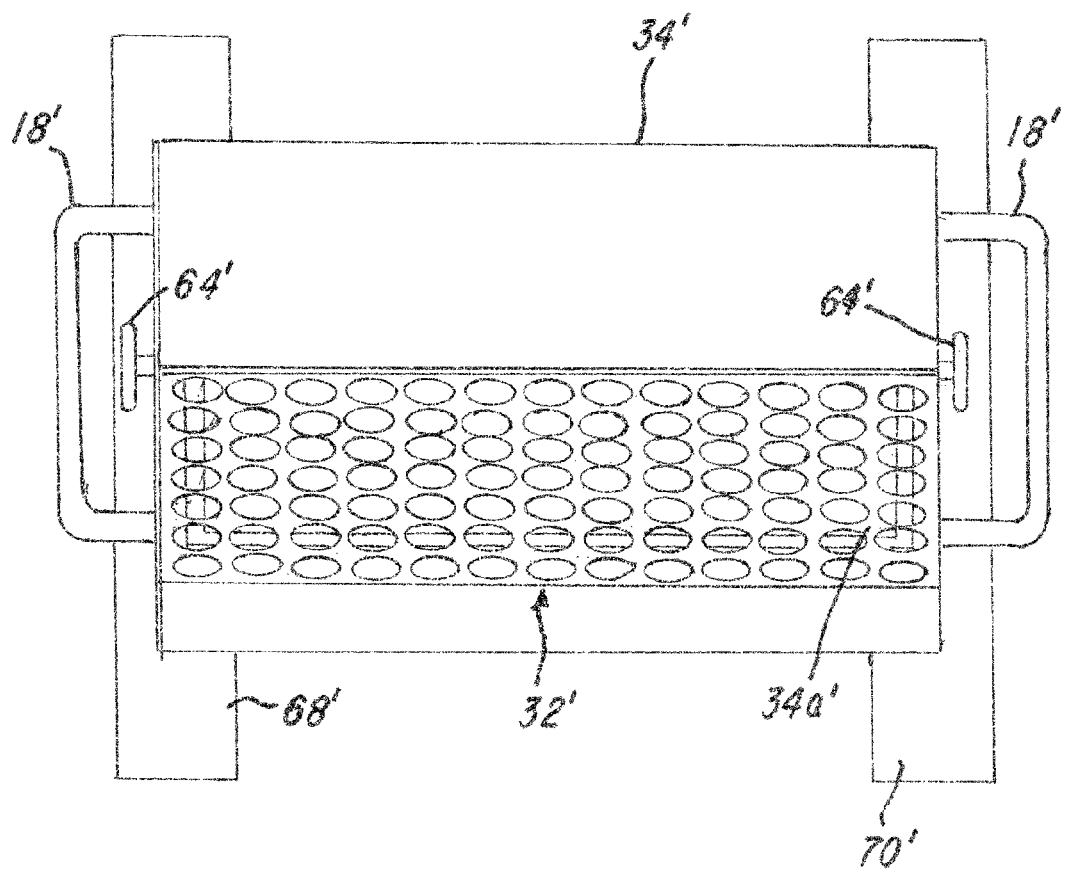
FIG. 10 is a plan view of the embodiment shown in FIG. 6.

A significant feature of the embodiments being described is that the radiation-transmissible media 46 are adapted to permit transmission of radiation from the radiation source 38 through the radiation-transmissible media 46 with the radiation source 38 providing an adequate amount of radiation appropriate to disinfect the fluid stream and at least one surface, such as surfaces 46a and 46b (FIG. 5A) of the radiation-transmissible media 46. In the illustration being described, the radiation-transmissible media 46 are generally tubular or circular quartz or silicate pieces, but they could comprise borosilicate, glass or transparent polymer. In one embodiment, quartz is used because it provides for maximum ultraviolet transmission through the radiation-transmissible media 46. As mentioned earlier herein, the purpose of the radiation-transmissible media 46 is to provide both mechanical filtration by physically capturing unwanted organisms on a surface, such as the surfaces 46a and 46b, of the radiation-transmissible media 46 as contaminants or pathogens 54 (FIG. 4) move through the fluid sterilization system 10.

In the illustrative embodiment shown in FIGS. 1-5, the generally rectangular frame or edge 38a is not permanently secured to the container 42, but, rather, the frame or edge 38a is aligned and situated such that the surface or edge 38a1 is received on and mates with the top surface or edge 34a, as illustrated in FIGS. 2-3A. This permits, among other things the top surface or edge 38a to be removably received on the container 42 as illustrated in FIG. 3A. This is advantageous because it permits the easy removal, charging or replacement of the radiation-transmissible media 46 into the storage unit 44 of the container 42. In the illustration being described, the container 42 and the frame or edge 38a may be manufactured from a metal, such as stainless steel or even a transparent material or mesh. A primary purpose of the container 42 is to contain the radiation-transmissible media 46 and to provide for fluid flow through the radiation-transmissible media 46 while allowing for penetration of the ultraviolet lamps 40 (labeled UV in FIG. 4) in the radiation-transmissible media 46 and the fluid stream (labeled AS in FIG. 4). Although not shown, another mesh, grate or screen may be situated between the edge 38a and the container 42 and between the edges 34a and 38a.

As illustrated in FIG. 4 and mentioned earlier herein, the primary purpose of the radiation-transmissible media 46 is to provide mechanical filtration by physically capturing organisms on the surfaces, such as surfaces 46a, 46b (FIG. 5A) of the radiation-transmissible media 46 as the contaminants or pathogens 54 pass through the fluid filtration assembly 34 as shown. Substantially simultaneously, the radiation-transmissible media 46 also permits the ultraviolet radiation from the lamps 40 to be transmitted therethrough so that the contaminants or pathogens 54 are subject to ultraviolet radiation. In the illustration being described, the radiation source 38 is situated in series or adjacent to the radiation-transmissible media 46 and directly in the fluid stream AS so that the contaminants or pathogens 54 are also exposed directly to ultraviolet light in the event the contaminants or pathogens 54 are not captured or interrupted by the radiation-transmissible media 46.

The radiation-transmissible media 46 may assume various shapes, sizes or configurations. In the illustration being described, the radiation-transmissible media 46 comprises a plurality of generally tubular one-half inch cylinders or tubular members 46c (FIG. 5), which is shown in an enlarged view in FIG. 5A. As mentioned earlier, each of the radiation-transmissible media 46 are transparent so that they permit radiation from the plurality of ultraviolet lamps 40 to pass therethrough and also radiating the contaminants or pathogens 54 on the outer surface 46a and the inner surface 46b and also the contaminants or pathogens 54 that remain in the fluid stream as they pass through the fluid filtration assembly 34. Note in FIG. 4 that as the contaminants or pathogens 54 pass through the bottom 42a of the container 42 and through the frame 38a of the radiation source 38, the radiation-transmissible media 46 interrupts the fluid stream AS and captures some of the contaminants or pathogens 54 on their surfaces 46a, 46b (FIG. 5A) so that radiation (labeled UV in FIG. 4) from the plurality of ultraviolet lamps 40 can radiate the contaminants or pathogens 54 as illustrated. Note that the contaminants or pathogens 54 are caught in the matrix of the radiation-transmissible media 46 and the ultraviolet irradiation also penetrates the matrix, thereby maximizing radiation exposure and killing the contaminants or pathogens 54. As alluded to earlier, the radiation-transmissible media 46 may be arranged such that they provide a matrix that is in a predetermined order, as illustrated in FIGS. 2 and 3A, or they may be arranged randomly with no particular order as illustrated in FIG. 3B.

It should also be understood that while the radiation-transmissible media 46 has been shown and described herein as being generally tubular, cylindrical, or spherical members 46c, the radiation-transmissible media 46 could comprise other shapes or a mixture of shapes, such as polygonal shapes, such as squares or rectangles, circular, spherical, elliptical, planar or other shapes and they may also be solid, tubular, or even non-tubular with through holes or apertures. It is also important to note that while the radiation-transmissible media 46 have been shown and described herein as being generally the same shape and size, it should be understood that the radiation-transmissible media 46, such as quartz media, could comprise different predetermined shapes and sizes. In other words, the radiation-transmissible media 46 does not have to be the same size and shape and could comprise different sizes or shapes. Also, while the radiation-transmissible media 46 has been shown as being generally cylindrical, spherical, tubular or hollow, it should be understood that they could comprise a solid shape, although the hollow shape is preferred because it increases the amount of surface area for receiving contaminants or pathogens 54 (FIG. 4) as they pass through the fluid filtration assembly 34.

Although not shown, the radiation-transmissible media 46 may be coated or doped with at least one or a plurality of ultraviolet emission material or a fluorescent material to facilitate irradiation of the contaminants or pathogens 54. For example, the coating or doping could be a UV fluorescent material that emits radiation to facilitate decontamination.

It should be understood that at least one of a size of the radiation-transmissible media 46 or a shape of the radiation-transmissible media 46 is selected in response to, for example, a velocity of the fluid stream AS (FIG. 4) that passes through the container 42 and through the fluid filtration assembly 34. In this regard, the at least one fan or blower 24 (FIG. 1), which is under the control of the control panel 20 and controller 22, may generate the fluid stream on the order of about 500 CFM. In the illustration being described, if the amount of fluid flow generated by the at least one fan or blower 24 decreases, then less radiation-transmissible media 46 may be needed. However, if fluid flow through the container 42 is increased, then it may be desirable to increase an amount of the radiation-transmissible media 46 contained in the storage area 44 of the container 42. This is easily done by removing the cover or hood 33, HEPA filter 36 and frame or edge 38a and by adding more radiation-transmissible media 46 into the storage area 44 of the container 42. Alternatively, the container 42 may be removed from the mobile housing unit 12 and the radiation-transmissible media 46 replaced or modified with new or different radiation-transmissible media 46, new radiation-transmissible media 46 or more radiation-transmissible media 46 may be added to the storage area 44 of the container 42. Thus, it should be appreciated that one advantageous feature of the embodiment being described is the ease with which the radiation-transmissible media 46 may be placed into or removed from the storage area 44.

In the illustration shown and described in FIGS. 1-5, it is important to note that the container 42 lies in a first generally planar imaginary plane and the radiation source 38 lies in a second generally planar imaginary plane as illustrated n FIGS. 2 and 3A. The first and second imaginary planes are generally parallel in the embodiment being described. Note also that the plurality of ultraviolet lamps 40 are arrayed in a linear or planar pattern in the second imaginary plane.

Again, it should be understood that the radiation-transmissible media 46, which in the embodiment being described is quartz media, is adapted and selected to vary at least one or all of a path of the fluid stream AS (FIG. 4), disrupt the fluid stream AS or slow a velocity of the fluid stream AS so that the contaminants or pathogens 54 in the fluid stream AS will either land on the surface, such as the surfaces 46a and 46b (FIG. 5A) of the radiation-transmissible media 46, or will be disrupted long enough so that the plurality of ultraviolet lamps 40 can irradiate the contaminants or pathogens 54. Thus, the fluid filtration assembly 34 causes the contaminants or pathogens 54 to have a longer exposure time to the radiation source 38 when compared to fluid filtration systems of the past, many of which only had a HEPA filter 36.

Returning to FIG. 1, the HEPA filter 36, radiation source 38 and fluid filtration assembly 34 may be removed from the mobile housing unit 12 by lifting it vertically (as illustrated in FIG. 1). First, the HEPA filter 36 is manually removed and the frame 38a of the radiation source 38 is removed. The container 42 may then be removed and serviced as mentioned earlier herein. After the fluid filtration assembly 34 is serviced or the HEPA filter 36 is serviced, the container 42 is returned to the mobile housing unit 12 and situated on the support surface or shelf 12d (FIG. 1) of the mobile housing unit 12 as illustrated in FIG. 1. As mentioned earlier, the support surface or shelf 12d provides a frame or support for supporting the container 42 and has an aperture (not shown) that permits fluid to flow through the support surface or shelf 12d and through the container 42, radiation source 38 and HEPA filter 36.

After the container 42 is situated on support surface or shelf 12d, the radiation source 38 may be positioned so that the edge 38a1 matingly aligns with and rests on the top surface or edge 34a. Thereafter, the HEPA filter 36 may be placed on the top edge 38b of the radiation source 38. The cover or hood 33 may then be removably mounted on the mobile housing unit 12 by situating it on the ledge 12b and support wall 12c as illustrated in FIG. 1.

If it is desired to service the fluid filtration assembly 34, for example, to replace the radiation-transmissible media 46, to replace a lamp 40, to add to the radiation-transmissible media 46, to remove or clean the radiation-transmissible media 46 or the like, then the cover or hood 33 (FIG. 1) may be removed from the mobile housing unit 12 so that the HEPA filter 36 can be removed from the frame 38a of the radiation source 38, thereby providing access to the container 42. As mentioned earlier, the container 42 could be serviced while in the mobile housing unit 12 or it can be manually removed and serviced outside of the mobile housing unit 12.

In the illustration being described, the mobile housing unit 12 and container 42 are stainless steel and may have one or more mirrored surfaces to facilitate reflection of the light from the lamps 40. Although the radiation source 38 has been shown and described as comprising ultraviolet lamps 40, it should be understood that other types of light or radiation may be provided, such as white light, electromagnetic energy or the like. It should be understood that the lamps 40 may be UV, fluorescent, LED, white light, or other sources of UV radiation and germicidal UVC wavelengths. The sources can be arranged such that adequate radiation reaches the radiation-transmissible media 46 and container 42 and the fluid flow therein.

During use, the user may grasp the handles 18 and move the mobile housing unit 12 to a desired location, such as a room in a hospital. The fluid sterilization system 10 is plugged into a conventional power source (not shown) with a plug (not shown) and the user uses the control panel 20 to use the fluid sterilization system 10. While the fluid sterilization system 10 is primarily intended for medical environments where disinfection of fluid is particularly desired, it should be understood that the fluid sterilization system 10 may be used in virtually any environment or room where it is desired to reduce the amount of contaminants or pathogens 54 in the fluid stream AS. While a primary embodiment illustrates the fluid sterilization system 10 as being mobile, it should be understood that the features of the embodiments being described herein could be used in a permanent structure, fixture or duct system. Also, it may be desirable to use features of the embodiments being described herein and with other types of fluid streams, such as in a water stream where it is desired to reduce or eliminate contaminants or pathogens in water.

FIGS. 6-10 illustrate another embodiment of the invention. Like parts are identified with the like part numbers, except a prime mark ("'") has been added. In this embodiment, the fluid filtration assembly 34' comprises the radiation-transmissible media 46' and radiation source 38' which are provided and located in a single assembly, unit or container 60'. In this embodiment, the container 60' has a footprint of about twelve inches by twelve inches. In this embodiment, note that the cover or hood 33' is slidably received on the housing wall 12*a*' until notched out areas 62' are received and supported by threaded knobs 64' which can be tightened to secure the cover or hood 33' onto the mobile housing unit 12' as illustrated in FIG. 6. In the illustration being described, the embodiment of FIGS. 6-10 comprises a plurality of supports 67' and 70' onto which the wheels 16' are mounted and which support and receive the mobile housing unit 12' as shown. In this regard, the mobile housing unit 12' is conventionally secured, such as by weld or by fasteners, to the supports 67' and 70'.

The housing wall 12a' comprises an aperture 92' defined by an interior wall 12e' as illustrated. In this embodiment, the mobile housing unit 12' comprises a pair of support surfaces or edges 66' and 68' for receiving and supporting the fluid filtration assembly 34' and HEPA filter 36', respectively.

Referring now to FIGS. 7-8, note that the support surface 66' comprises an aperture 72' (FIG. 7) that is in communication with an outlet 74' of the at least one blower 24' as shown in FIG. 7. A locator or drop-in frame 76' is conventionally secured, such as by weld or fasteners, to the support surfaces 66'. The locator or drop-in frame 76' comprises a locator wall or surface 76a' that comprises a locator edge 76a1' that defines a locator or frame aperture adapted and sized to generally complement the size and shape of a housing or container wall 80' of the fluid filtration assembly 82' of the embodiment shown in FIG. 8. Advantageously, the locator or drop-in frame 76' enables a user to drop the container 60' having the fluid filtration assembly 82' onto the support surface 66' which causes the container 60' to be generally aligned with the aperture so that the at least one blower 24' can blow fluid therethrough and through the HEPA filter 36' and ultimately out the perforated grate or screen 33a' of the cover or hood 33'.

Note that the generally L-shaped joining wall portions 76b' join the frame or locator wall or surface 76a' to the support surface 66'.

A primary feature of this embodiment is the fluid filtration assembly 82' has a radiation source 38' and radiation-transmissible media 46' all located within the same housing or container 60' as shown. In this regard, the frame 46 of the embodiment shown in FIG. 3A is not integral with the container 42 in FIG. 3A. In contrast, the container 60' is adapted to house and support the lamps 40'. The container 60' comprises a plurality of generally circular apertures 84' in the generally square housing wall that are adapted in size to receive and support the lamps 40', which protrude through the container 60' as illustrated in FIG. 8.

The lamps 40' in this embodiment are coupled to the ballast 52' and under the control of the control panel 20' and controller 22'. It should be understood that the container 60' comprises a perforated or mesh screen floor 88' that supports the at least one or plurality of radiation-transmissible media 46'. As with the prior embodiment, the radiation-transmissible media 46' may be arranged and stacked in a predetermined order, or alternatively, they may be situated in the area 90' of the container 60' in a random order, which sometimes occurs when the radiation-transmissible media 46' is "poured" into the container 60'.

In general, the area 90' of the container 60' is filled with the radiation-transmissible media 46' and then the lamps 40' of the radiation source 38' are situated in the container 60' as illustrated. As with the embodiment described earlier herein, the lamps 40' may be situated in a linear array and in the same plane or, alternatively, they could be situated at different orientations with respect to the radiation-transmissible media 46' or with respect to each other.

After the container 60' and lamps 40' are assembled as illustrated in FIG. 8, a mesh screen 108" may be placed over the container 60'. Thereafter, the container 60' is manually lifted and inserted into the mobile housing unit 12' in the direction of arrow B in FIG. 7 until it is received in the locator frame 76' as shown. After the fluid filtration assembly 34' of the embodiment being described in FIGS. 6-10 is situated in the mobile housing unit 12', the HEPA filter 36' may be situated on the support surface or ledge 68'. In this regard, notice that the support surface or edge 68' defines a generally planar surface 68a' (FIG. 7) that has an interior wall 68a1' that defines an aperture 92' through which the fluid stream may pass through the HEPA filter 36'. Although not shown, the mobile housing unit 12' may comprise a flange or locator frame (not shown) similar to the frame 76' for locating the HEPA filter 36' in aligned relationship with the aperture 92'.

One advantageous feature of the illustration being described relative to FIGS. 6-10 is that the radiation source 38' and radiation-transmissible media 46' are located in a single unit or container 60' that can be placed into and removed from the mobile housing unit 12'.

Another advantageous feature of both the embodiments of FIGS. 1-5 and FIGS. 6-10 is the ease with which the units can be transported and placed into an area where it is desired to filter and decontaminate the fluid. In this regard, the handles 18 and 18' may be used transport or place or move the fluid sterilization system 10 and 10' from one area to another, such as from one hospital room to another hospital room or the like.

While the embodiments of FIGS. 1-10 illustrate generally square or rectangular fluid sterilization systems, it should be understood that the fluid filtration assembly could be provided in other configurations and FIGS. 11-13 illustrate one such configuration. In FIGS. 11-13, like parts are identified with the like part numbers, except a double prime mark ("''") has been added. As illustrated in FIG. 11, a generally cylindrical container 100" is provided which has a generally cylindrical housing or wall 102' having a bottom surface 104" and a top surface 106" which are mirror images of each other. Note that the top and bottom surfaces 104" and 106" comprise a mesh screen 108" that permits fluid to flow through the container 100". In this embodiment, the radiation-transmissible media 46" are generally circular or spherical solid glass or quartz media that are stored or contained within a generally circular glass or transparent wall 110" which cooperates with the top and bottom surfaces 104" and 106" to contain the radiation-transmissible media 46".

Around the glass or transparent wall 102" a generally circular array of lamps 40" is provided. Note therein that the lamps 40" are situated in a generally circular array around the glass or transparent wall 110" and irradiate the fluid stream and the radiation-transmissible media 46" as shown.

Thus, it should be understood that the embodiments being described herein that the fluid filtration assembly 34" may have the container 42" and radiation-transmissible media 46" housed separately, as illustrated in FIGS. 1-5 or a one-piece housing in one unit (FIGS. 7-13). Also, the containers 42, 60' and 102" may be of a generally polygonal, square or rectangular shape or it could comprise a other shapes, such as circular, spherical or elliptical. The fluid filtration assembly 34, 34', 34" may also be elongated as shown in FIG. 11 and/or the one-piece construction or assembly as illustrated in the embodiments of FIGS. 6-10 and 11. Also, the container 42 may be provided in other shapes and sizes, such as in the generally circular shape of the container 100" shown in FIG. 11.

The radiation source 38, 38', 38" and lamps 40, 40', 40" shown in FIGS. 11-13 may be provided in different arrays other than the linear or planar arrays shown in FIGS. 2 and 8, such as in the generally circular array. Also, note that the general axes of the lamps 40, 40' and 40" may be arranged such that their axes are generally perpendicular to the fluid stream flow as illustrated in FIGS. 2 and 8 and directly in the fluid stream flow as shown. Alternatively, the lamps 40, 40' and 40" may be placed such that their axes are generally parallel to the fluid stream flow as illustrated in FIG. 11. The axes of lamps 40, 40' and 40" do not have to be parallel to each other.

It should be understood that for the embodiment of FIGS. 11-13, the supports, such as the support surface 66' in FIG. 8, is adapted and modified to have a circular opening that generally corresponds to the circular wall 112" (FIG. 11). The same advantageous features described earlier herein relative to FIGS. 1-10 also apply to the embodiment of FIGS. 11-13. The fluid filtration assembly 102" may be easily removed or inserted in the housing 12 of the fluid sterilization system 10 with appropriate modifications to the surface 12d.

The fluid sterilization system 10, 10', 10" is intended primarily for use in filtering fluid and for use in medical and hospital environments as mentioned earlier, but it could be used in other environments, such as home, commercial, office, or highly populated or traffic areas, like airports or restaurants.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:

1. A fluid sterilization system comprising:
a container;
radiation-transmissible media situated in said container; and
a radiation source;
said radiation-transmissible media being adapted to provide both mechanical filtration by physically capturing organisms as they are carried through the container in a fluid stream and substantially capturing organisms as they are carried through the container in a fluid stream and through said radiation-transmissible media, said radiation being an appropriate amount to disinfect said fluid stream and at least one surface of said radiation-transmissible media;
said radiation-transmissible media comprising a plurality of discrete and individual media that are randomly situated and distributed in said container and confined by said container, each of said plurality of discrete and individual media being tubular and having a wall having an inner surface and an outer surface, said inner surface defining a hollow passageway;
wherein said container is generally planar and lies in a first imaginary plane, said radiation source comprises a plurality of ultraviolet lamps arrayed in a linear pattern in a second imaginary plane above said container.

2. The fluid sterilization system as recited in claim 1 wherein said radiation-transmissible media comprises at least one of quartz media, glass or polymer.

3. The fluid sterilization system as recited in claim 2 wherein said radiation-transmissible media comprises a plurality of media, each of which are generally the same size.

4. The fluid sterilization system as recited in claim 2 wherein said radiation-transmissible media comprises a plurality of media having different sizes or dimensions.

5. The fluid sterilization system as recited in claim 1 wherein said radiation-transmissible media comprises quartz media.

6. The fluid sterilization system as recited in claim 5 wherein said container comprises a plurality of said quartz media.

7. The fluid sterilization system as recited in claim 6 wherein said plurality of said quartz media comprises different predetermined shapes.

8. The fluid sterilization system as recited in claim 7 wherein said predetermined shape is at least one of a circular shape, a cylindrical shape, a spherical shape, or a polygonal shape.

9. The fluid sterilization system as recited in claim 6 wherein said plurality of said quartz media comprises generally the same predetermined shape.

10. The fluid sterilization system as recited in claim 9 wherein said predetermined shape is at least one of a circular shape, a cylindrical shape, a spherical shape, or a polygonal shape.

11. The fluid sterilization system as recited in claim 10 wherein said plurality of discrete and individual media comprises a plurality of said quartz media.

12. The fluid sterilization system as recited in claim 9 wherein said predetermined shape is coated or doped with at least one of an ultraviolet emission material or a fluorescent material.

13. The fluid sterilization system as recited in claim 5 wherein at least one of a size or amount of said radiation-transmissible media is adapted to at least one of vary a path of said fluid stream, disrupt said fluid stream, or slow a velocity of said fluid stream.

14. The fluid sterilization system as recited in claim 1 wherein said radiation source is at least one of white light or an ultraviolet radiation source.

15. The fluid sterilization system as recited in claim 1 wherein said radiation source is an ultraviolet radiation source.

16. The fluid sterilization system as recited in claim 1 wherein said at least one of a size of said media or a number of said media are selected in response to a velocity of said fluid stream through said container.

17. The fluid sterilization system as recited in claim 1 wherein said first and second imaginary planes are generally parallel.

18. The fluid sterilization system as recited in claim 1 wherein said container is generally cylindrical and said radiation source comprises a plurality of ultraviolet lamps arrayed generally radially around said container.

19. The fluid sterilization system as recited in claim 1 wherein said radiation source comprises a plurality of ultraviolet lamps arranged in a generally circular array, wherein said plurality of ultraviolet lamps generally surround said radiation-transmissible media.

20. The fluid sterilization system as recited in claim 1 wherein said container is a one-piece construction that houses both said radiation-transmissible media and said radiation source.

21. The fluid sterilization system as recited in claim 1 wherein said container is adapted to receive said radiation-transmissible media and a second member comprises a frame that receives and supports said radiation source.

22. The fluid sterilization system as recited in claim 21 wherein said second member is adjacent to said radiation-transmissible media either upstream or downstream of said radiation-transmissible media.

23. The fluid sterilization system as recited in claim 1 wherein said radiation-transmissible media is substantially transparent to light.

24. A fluid sterilization system comprising:
a container;
radiation-transmissible media situated in said container; and a radiation source;

said radiation-transmissible media being adapted to provide both mechanical filtration by physically capturing organisms as they are carried through the container in a fluid stream and substantially capturing organisms as they are carried through the container in a fluid stream and through said radiation-transmissible media, said radiation being an appropriate amount to disinfect said fluid stream and at least one surface of said radiation-transmissible media;

said radiation-transmissible media comprising a plurality of discrete and individual media that are randomly situated and distributed in said container and confined by said container, each of said plurality of discrete and individual media being tubular and having a wall having an inner surface and an outer surface, said inner surface defining a hollow passageway;

wherein said container is generally planar and lies in a first imaginary plane, said radiation source comprises a plurality of ultraviolet lamps arrayed in a linear pattern in a second imaginary plane within or adjacent to said container; said system further comprising:

a mobile housing adapted to house said container containing said plurality of ultraviolet lamps, said plurality of said radiation-transmissible media and said plurality of ultraviolet lamps;

said mobile housing having at least one fan or blower and a controller for controlling operation of said at least one fan or blower and said plurality of ultraviolet lamps.

25. The fluid sterilization system as recited in claim 24 wherein said mobile housing comprises a housing having at least one locator frame for removably locating said container to a desired position in said housing such that said radiation-transmissible media interrupts a fluid stream.

26. A filtration assembly for use in a fluid filtration system, said filtration assembly comprising:

a container; and radiation-transmissible media situated in said container;

said container being adapted to be situated in said fluid filtration system in proximate relationship to a radiation source to provide both mechanical filtration by physically capturing organisms as they are carried through the container in a fluid stream and substantially simultaneously permitting transmission of radiation from said radiation source through said radiation-transmissible media, said radiation being an appropriate amount to disinfect said fluid stream and at least one surface of said radiation-transmissible media;

said radiation-transmissible media comprising a plurality of discrete and individual media that are randomly situated and distributed in said container and confined by said container, each of said plurality of discrete and individual media being tubular and having a wall having an inner surface and an outer surface, said inner surface defining a hollow passageway;

wherein said container is generally planar and lies in a first imaginary plane, said radiation source comprises a plurality of ultraviolet lamps arrayed in a linear pattern in a second imaginary plane in said fluid filtration system, said second imaginary plane being generally parallel to said first imaginary plane after said container is situated in said fluid filtration system.

27. The filtration assembly as recited in claim 26 wherein said radiation-transmissible media comprises at least one of quartz media, glass or polymer.

28. The filtration assembly as recited in claim 27 wherein said radiation-transmissible media comprises different predetermined shapes.

29. The filtration assembly as recited in claim 27 wherein said radiation-transmissible media comprises generally the same predetermined shape.

30. The filtration assembly as recited in claim 29 wherein said predetermined shape is at least one of a circular shape, a cylindrical shape, a spherical shape, or a polygonal shape.

31. The filtration assembly as recited in claim 29 wherein said predetermined shapes are coated or doped with at least one of an ultraviolet emission material or a fluorescent material.

32. The filtration assembly as recited in claim 27 wherein said at least one of a size of said radiation-transmissible media or a number of said radiation-transmissible media are selected in response to a velocity of said fluid stream through said container.

33. The filtration assembly as recited in claim 26 wherein said radiation source is a ultraviolet radiation source.

34. The filtration assembly as recited in claim 26 wherein said radiation-transmissible media is coated or doped with at least one of an ultraviolet emission material or a fluorescent material.

35. The filtration assembly as recited in claim 26 wherein said container is generally cylindrical and said radiation source comprises a plurality of ultraviolet lamps arrayed generally radially around said container after said container is situated in said fluid filtration system.

36. The filtration assembly as recited in claim 26 wherein said radiation-transmissible media are generally the same size.

37. The filtration assembly as recited in claim 26 wherein said radiation-transmissible media have different sizes or dimensions.

38. The filtration assembly as recited in claim 26 wherein at least one of a size of said radiation-transmissible media is adapted to at least one of vary a path of said fluid stream, disrupt said fluid stream, or slow a velocity of said fluid stream.

39. The filtration assembly as recited in claim 26 wherein said radiation source comprises a plurality of ultraviolet lamps arranged in a generally circular array, wherein said plurality of ultraviolet lamps generally surround said radiation-transmissible media.

40. The filtration assembly as recited in claim 26 wherein said container is a one-piece construction that houses both said radiation-transmissible media and said radiation source.

41. The filtration assembly as recited in claim 26 wherein said container is adapted to receive said radiation-transmissible media and a second member comprises a frame that receives and supports said radiation source.

42. The filtration assembly as recited in claim 41 wherein said second member is stacked on said radiation-transmissible media and downstream of said radiation-transmissible media.

43. A filtration assembly for use in a fluid filtration system, said filtration assembly comprising:

a container; and radiation-transmissible media situated in said container;

said container being adapted to be situated in said fluid filtration system in proximate relationship to a radiation source to provide both mechanical filtration by physically capturing organisms as they are carried through the container in a fluid stream and substantially simultaneously permitting transmission of radiation from said radiation source through said radiation-transmissible media, said radiation being an appropriate amount to disinfect said fluid stream and at least one surface of said radiation-transmissible media;

said radiation-transmissible media comprising a plurality of discrete and individual media that are randomly situated and distributed in said container and confined by said container, each of said plurality of discrete and individual media being tubular and having a wall having an inner surface and an outer surface, said inner surface defining a hollow passageway;

wherein said fluid filtration system comprises:

a mobile housing adapted to receive and house said container, said mobile housing being moveable by hand and containing a plurality of ultraviolet lamps arranged in a second imaginary plane such that they become operatively associated with said container after said container is mounted in said mobile housing;

said mobile housing further comprising:

at least one fan or blower for generating said fluid stream through said mobile housing; and a controller for controlling operation of said at least one fan or blower and said plurality of ultraviolet lamps.

44. The filtration assembly as recited in claim 43 wherein said mobile housing comprises a housing having at least one locator frame for removably locating said container to a desired position in said housing such that said radiation-transmissible media interrupts a fluid stream.

45. A filtration assembly for use in a fluid filtration system, said filtration assembly comprising:

a container; and radiation-transmissible media situated in said container;

said container being adapted to be situated in said fluid filtration system in proximate relationship to a radiation source to provide both mechanical filtration by physically capturing organisms as they are carried through the container in a fluid stream and substantially simulataneously permitting transmission of radiation from said radiation source through said radiation-transmissible media, said radiation being an appropriate amount to disinfect said fluid stream and at least one surface of said radiation-transmissible media;

said radiation-transmissible media comprising a plurality of discrete and individual media that are randomly situated and distributed in said container and confined by said container, each of said plurality of discrete and individual media being tubular and having a wall having an inner surface and an outer surface, said inner surface defining a hollow passageway;

wherein said container is generally planar and lies in a first imaginary plane, said radiation source comprises a plurality of ultraviolet lamps arrayed in a linear pattern in a second imaginary plane above said container; said system further comprising;

a mobile housing adapted to house said container containing said plurality of ultraviolet lamps, a plurality of quartz media and said plurality of ultraviolet lamps;

said mobile housing having at least one fan or blower and a controller for controlling operation of said at least one fan or blower and said plurality of ultraviolet lamps.

* * * * *

UNITED STATES PATENT AND TRADEMARK OFFICE
CERTIFICATE OF CORRECTION

PATENT NO.        : 9,457,119 B2
APPLICATION NO.   : 13/838367
DATED             : October 4, 2016
INVENTOR(S)       : David Louis Kirschman It is certified that error appears in the above-identified patent and that said Letters Patent is hereby corrected as shown below:

In the Claims

Column 11, Lines 36-38, delete "capturing organisms as they are carried through the container in a fluid stream and", insert --simultaneously permitting transmission of radiation from said radiation source-- therefor.

Column 13, Lines 5-7, delete "capturing organisms as they are carried through the container in a fluid stream and", insert --simultaneously permitting transmission of radiation from said radiation source-- therefor.

Column 13, Lines 45, 46, delete "simulataneously", insert --simultaneously-- therefor.

Column 14, Line 65, 66, delete "simulataneously", insert --simultaneously-- therefor.

Column 16, Line 7, 8, delete "simulataneously", insert --simultaneously-- therefor.

Signed and Sealed this
Twenty-seventh Day of December, 2016

Michelle K. Lee
*Director of the United States Patent and Trademark Office*